United States Patent [19]

Findeisen et al.

[11] 4,302,583

[45] Nov. 24, 1981

[54] PROCESS FOR THE PREPARATION OF ACYL CYANIDES

[75] Inventors: Kurt Findeisen, Odenthal; Karl-Heinz Linker, Leverkusen, both of Fed. Rep. of Germany

[73] Assignee: Bayer Aktiengesellschaft, Leverkusen, Fed. Rep. of Germany

[21] Appl. No.: 33,606

[22] Filed: Apr. 25, 1979

[30] Foreign Application Priority Data

May 11, 1978 [DE] Fed. Rep. of Germany ....... 2820575

[51] Int. Cl.³ ................. C07D 307/30; C07D 207/10; C07D 253/06; C07D 235/04

[52] U.S. Cl. ................. 544/176; 260/545 R; 260/347.3; 260/326.5 J; 544/182; 548/325; 548/331; 548/343; 548/378; 548/262; 548/255; 548/128; 548/225; 548/240; 546/245

[58] Field of Search ......... 260/545 R, 347.3, 326.5 J; 544/176, 182; 546/245; 548/325, 331, 343, 378, 262, 255, 128, 225, 240

[56] References Cited

U.S. PATENT DOCUMENTS 2,426,014 8/1947 Gresham .................... 260/545 R
3,234,265 2/1966 Krekeler et al. ............. 260/545 R

FOREIGN PATENT DOCUMENTS 1266751 2/1963 Fed. Rep. of Germany ... 260/545 R
435235 5/1967 Switzerland .................. 260/545 R
1247929 9/1971 United Kingdom ............ 260/545 R

OTHER PUBLICATIONS

Angewandte Chemie, 68, Johrgang, No. 13, pp. 425–448, Jul. 7, 1956.

Berichte Deut. Chemische Gesell., 18, 256 (1885).

Primary Examiner—Henry R. Jiles
Assistant Examiner—Robert C. Whittenbaugh
Attorney, Agent, or Firm—Sprung, Felfe, Horn, Lynch & Kramer

[57] ABSTRACT

Novel process for the preparation of a monomeric acyl cyanide of the general formula

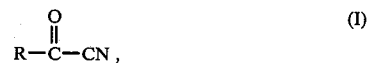
(I)

in which R represents optionally substituted alkyl with up to 8 carbon atoms, optionally substituted cycloalkyl with 3 to 12 carbon atoms, optionally substituted aryl or an optionally substituted 5-membered or 6-membered heterocyclic radical, which optionally can be fused with a benzene ring, which process comprises heating the corresponding dimeric acyl cyanide of the general formula

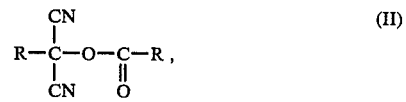
(II)

in which R has the meaning stated above, to a temperature of from 50° to 300° C. in the presence of a compound having a basic reaction and rapidly removing the monomeric acyl cyanide (I) formed from the reaction mixture.

36 Claims, No Drawings

PROCESS FOR THE PREPARATION OF ACYL CYANIDES

The present invention relates to a process for the preparation of certain monomeric acyl cyanides from dimeric acyl cyanides.

It has already been known for a long time that monomeric acyl cyanides are dimerized to correspondingly substituted O-acyl-tartronic acid dinitriles ("dimeric acyl cyanides") under the influence of metallic sodium (see J. prakt. Chem. (2), volume 39, page 260 (1889)) or potassium hydroxide (Liebigs Ann. Chem. 120, page 334 (1861)).

It is furthermore known that dimeric acyl cyanides are formed when certain carboxylic acid derivatives, such as carboxylic acid chlorides or anhydrides, are reacted with hydrocyanic acid in the presence of a basic catalyst (see Angew. Chem. 68, page 434–435 (1956)). In the synthesis of the monomeric acyl cyanides, it is also frequently impossible to suppress the formation of dimeric acyl cyanides, which in this case are undesired, and this then leads to losses in yield, to a greater or lesser extent, of monomeric acyl cyanide (see Angew. Chem. 68, page 425–426 (1956)).

The present invention provides a process for the preparation of a monomeric acyl cyanide of the general formula

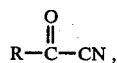
(I)

in which R represents optionally substituted alkyl with up to 8 carbon atoms, optionally substituted cycloalkyl with 3 to 12 carbon atoms, optionally substituted aryl or an optionally substituted 5-membered or 6-membered heterocyclic radical, which optionally can be fused with a benzene ring,
in which process the corresponding dimeric acyl cyanide of the general formula

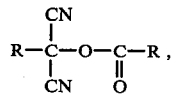
(II)

in which R has the meaning stated above, is heated to a temperature of from 50° to 300° C. in the presence of a compound having a basic reaction and if appropriate in the presence of a diluent, and the monomeric acyl cyanide (I) formed is removed from the reaction medium as rapidly as possible, preferably by distillation, if appropriate under reduced pressure. As has furthermore been found, the dimeric acyl cyanides (II) can also be employed as mixtures with the particular corresponding monomeric acyl cyanides (I); such mixtures are obtained when carboxylic acid derivatives are reacted with hydrocyanic acid in the presence of basic catalysts by previously known processes (see Angew. Chem. 68, page 425–448 (1956)).

It is to be described as decidedly surprising, with regard to the state of the art, that monomeric acyl cyanides of the formula (I) are accessible in high yield and excellent purity by the process according to the invention by splitting the corresponding dimeric acyl cyanides (II), since it was known that, conversely, monomeric acyl cyanides are converted into dimeric acyl cyanides in the presence of basic catalysts; the reversal of this reaction, that is to say the smooth splitting of the dimeric acyl cyanides to monomeric acyl cyanides, under very similar conditions could in no way be expected. In particular, it was also unforeseeable that no resinous products are formed when the reaction mixture is warmed in the presence of a compound having a basic reaction (see Liebigs Annalen der Chemie 287, page 306 (1895)).

The process according to the invention has a number of advantages. Thus, it is not limited to the synthesis of a few particular compounds, but has a very broad application. Furthermore, the process according to the invention can give acyl cyanides in virtually quantitative yields and in excellent purity, free from byproducts which are troublesome or pollute the environment. A further substantial advantage of the new process is that the working up presents no problems: the monomeric acyl cyanides desired are immediately obtained in the pure form from the reaction mixture by distillation.

An additional, quite decisive advantage of the process according to the invention is that the dimeric acyl cyanides (II) do not have to be employed in the pure form, but can be employed as a mixture with the particular corresponding monomeric acyl cyanide (I). Such (I)/(II) mixtures are obtained when [with the aim of preparing monomeric acyl cyanides] the corresponding acyl chlorides are reacted with hydrocyanic acid and pyridine, as an acid-binding agent, in accordance with the state of the art (see J. Chem. Soc. [London] 127, page 1,635 (1925)). The proportion of dimeric acyl cyanide (II) which is obtained as an undesired by-product in the previously known process can be very considerable (up to about 70%) and accordingly decreases the yield of monomeric acyl cyanide (I). If the previously known process is now followed by the process according to the invention, before separating, by distillation, the monomer/dimer mixture always obtained in this previously known process, it is also possible to convert acyl chlorides and other acid derivatives into monomeric acyl cyanides (I) with excellent yields, without intermediate isolation of the dimeric acyl cyanides (II).

If dimeric benzoyl cyanide is used as the starting material and sodium cyanide is used as the catalyst, the course of the reaction in the process according to the invention can be represented by the equation which follows:

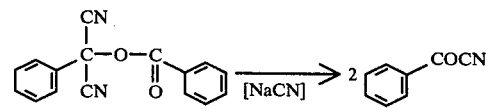

The formula (II) provides a general definition of the dimeric acyl cyanides used as the starting substances. In this formula, R preferably represents straight-chain or branched alkyl with 2 to 5 carbon atoms, which may optionally carry one or more substituents selected independently from aryl with 6 to 10 carbon atoms (preferably phenyl) [which aryl may carry one or more substituents selected independently from $C_1$–$C_4$ alkyl, $C_1$–$C_4$ alkoxy, $C_2$–$C_4$ carbalkoxy and halogen (especially chlorine, bromine or fluorine)], alkoxy with 1 to 4 carbon atoms, carbalkoxy with 1 to 4 carbon atoms in the alkoxy group, nitro, nitrile and halogen (for example fluorine, chlorine, bromine or iodine); cycloalkyl which has 5 or 6 carbon atoms in the ring system and which optionally may carry one or more substituent selected independently from alkyl, alkoxy or carbalkoxy with in each case up to 4 carbon atoms, nitro, nitrile and halogen (for example fluorine, chlorine and bromine); phenyl or naphthyl, either of which optionally may carry one or more substituents selected independently from alkyl, alkoxy and carbalkoxy with in each case up to 4 carbon atoms, nitro, nitrile and halogen (for example fluorine, chlorine and bromine); or a 5-membered or 6-membered heterocyclic radical which can contain 1 to 3 hetero-atoms in the ring, selected from oxygen, sulphur and nitrogen atoms, and can also be fused with a benzene ring, the heterocyclic radical optionally carrying one or more substituents selected independently from alkyl, alkoxy and carbalkoxy with in each case up to 4 carbon atoms, nitro, nitrile and halogen. Examples which may be mentioned of particularly suitable heterocyclic radicals are: morpholinyl, imidazolyl, pyrazolyl, pyrrolyl, isoxazolyl, piperidinyl, oxazolyl, 1,2,4-triazol-1-yl, 1,2,4-triazol-4-yl, 1,2,3-triazolyl, 1,2,4-thiadiazol-2-yl, benzimidazolyl and furanyl.

The dimeric acyl cyanides used as the starting substances are known, or they can be prepared by known processes (Angew. Chemie 68, page 425–435 (1956); see also under the preparative examples herein).

Specific preferred examples which may be mentioned of dimeric acyl cyanides of the formula (II) are the dimers of the following acyl cyanides: acetyl cyanide, propionyl cyanide, pivaloyl cyanide, cyclohexanecarboxylic acid cyanide, cyclopentanecarboxylic acid cyanide, benzoyl cyanide, m-chlorobenzoyl cyanide, 3,5-dichlorobenzoyl cyanide, naphthalene-1-carboxylic acid cyanide and 1-phenyl-5-pyrazolone-3-carboxylic acid cyanide. Dimeric pivaloyl cyanide and dimeric benzoyl cyanide may be mentioned as particularly preferred starting compounds.

Specific examples of compounds having a basic reaction which are to be employed according to the invention are the following substances: alkali metal salts (especially the sodium salts and potassium salts) of aliphatic, cycloaliphatic and aromatic carboxylic acids (for example sodium acetate and sodium benzoate, and the sodium salts of pivalic acid and of cyclohexylglyoxylic acid), alkali metal cyanides and complex cyanides (for example sodium cyanide, potassium cyanide, sodium cyanozincate, potassium cyanozincate, sodium cyanocuprate and potassium cyanocuprate), tertiary amines (for example triethylamine, dimethylbenzylamine, 1,4-diazabicyclo-(2.2.2)-octane, 1,8-diazabicyclo-(5.4.0)-undec-7-ene, 1,5-diaza-bicyclo-(4.3.0)-non-5-ene, pyridine and quinoline), alkali metal hydroxides and alkaline earth metal hydroxides (such as sodium hydroxide, potassium hydroxide, calcium hydroxide and barium hydroxide), and alcoholates and phenolates (for example, sodium methylate, sodium ethylate, potassium tert.-butylate and sodium phenolate). Particularly preferred bases are sodium cyanide, potassium cyanide, sodium acetate, potassium acetate, sodium benzoate, potassium benzoate, and the sodium salt and potassium salt of pivalic acid.

Possible diluents which can be employed in carrying out the process according to the invention are all the inert organic solvents which do not undergo a chemical reaction with the acyl cyanides and have boiling points at least 20° C. higher than that of the acyl cyanide formed. Examples of such solvents are the xylenes, such as o-xylene, chlorobenzene, o-dichlorobenzene, the trichlorobenzenes, nitrobenzene, tetramethylene sulphone, hexamethylphosphoric acid triamide, benzonitrile, benzyl cyanide, acetic anhydride, pivalic acid anhydride, cyclohexanecarboxylic acid anhydride, benzoic acid anhydride and benzoic acid methyl ester.

However, it is also possible, in principle, to carry out the reaction according to the invention without a diluent.

The reaction temperature can be varied within a substantial range. In general, the reaction is carried out at temperatures between 50° and 300° C., preferably between 80° and 250° C. and especially between 100° and 220° C. It is most appropriate to carry out the reaction below the boiling point of the dimeric acyl cyanide to be split and above the boiling point of the monomeric acyl cyanide.

The process according to the invention is carried out either under normal pressure or under reduced pressure, depending on the boiling point of the monomeric acyl cyanide formed. It is advisable to remove higher-boiling acyl cyanides from the reaction mixture by vacuum distillation. In these cases, the reaction is carried out in the pressure range down to about 0.1 mbar.

In carrying out the process according to the invention, the compounds having a basic reaction are employed in catalytic amounts; in general 0.01 to 0.2 mole, preferably 0.05 to 0.1 mole, of the compound having a basic reaction is employed per mole of dimeric acyl cyanide (II).

The process is most appropriately carried out by heating the reaction mixture to the reaction temperature under normal pressure or under appropriately reduced pressure, depending on the boiling point of the monomeric acyl cyanide of the formula (I) to be prepared. In this procedure, the acyl cyanide formed is continuously distilled off from the reaction mixture and thereby isolated. In most cases, further purification is not necessary; however, the acyl cyanides obtained can be re-distilled and/or recrystallised if desired.

If the starting material is not a pure dimeric acyl cyanide (II), but a mixture of a monomeric acyl cyanide and the corresponding dimeric acyl cyanide is first prepared in a manner which is known from the literature, it is most appropriate to add a catalytic amount of a compound having a basic reaction before the distillation and then (if appropriate after removing the diluent) to heat the mixture to the reaction temperature or boiling point, if appropriate under reduced pressure. The pure monomeric acyl cyanide (I) is again isolated by distillation.

In a preferred process variant, the reaction according to the invention can also be carried out continuously.

The acylcyanides of the formula (I) which can be prepared by the process according to the invention are valuable starting substances, for example for the synthesis of 1,2,4-triazin-5-ones, which possess outstanding herbicidal properties (see German Offenlegungsschrift (German Published Specification) No. 2,224,161).

Thus, for example, 3-methyl-4-amino-6-phenyl-1,2,4-triazin-5-one of the formula

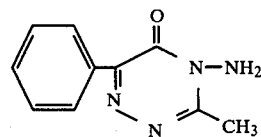

can be prepared by reacting benzoyl cyanide with ethanol in the presence of concentrated hydrochloric acid in a first stage and reacting the phenylglyoxylic acid ethyl ester thereby formed with acetyl hydrazine in a second stage, whereupon (ethyl 1-phenylglyoxylate)-2-acetyl-hydrazone is formed, and is converted into the above-mentioned end product with hydrazine hydrate in the presence of pyridine in a third stage. This multi-stage synthesis can be represented by the reaction scheme which follows:

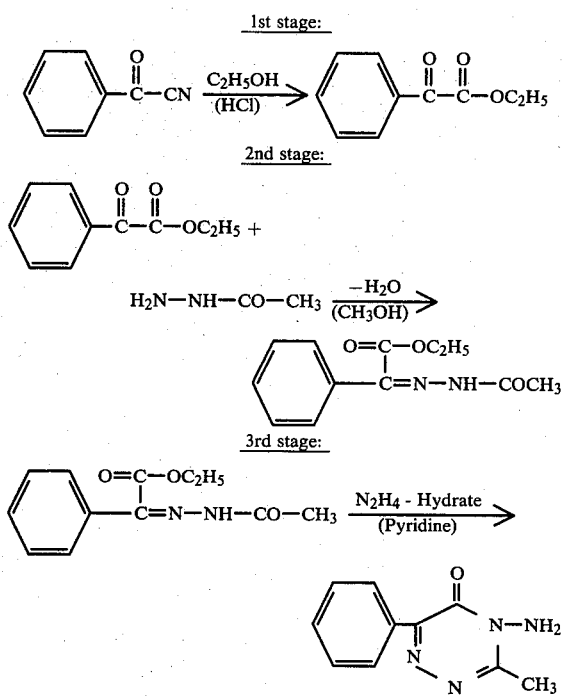

The process according to the invention is illustrated by the following preparative examples:

EXAMPLE 1

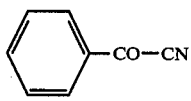

2 g of sodium cyanide were added to 131 g (0.5 mol) of dimeric benzoyl cyanide in a 250 ml three-necked flask provided with a stirrer, a thermometer and a small distillation column with a distillation attachment, and the mixture was warmed slowly under a water-pump vacuum (16 mbars). At an internal temperature of 160° to 165° C., the monomeric benzoyl cyanide began to distil into the receiver. The internal temperature was increased slowly to 200° C., whereupon further benzoyl cyanide was distilled off (overhead temperature: 92° to 130° C./16 mbars).

Yield: 122 g of pure benzoyl cyanide (93% of theory); boiling point: 87° to 89° C. under 17.3 mbars; melting point: 32° C.

EXAMPLE 2

3 g of potassium cyanide were added to 131 g (0.5 mol) of dimeric benzoyl cyanide analogously to Example 1. The reaction and working up were likewise carried out according to Example 1.

Yield: 123 g of pure benzoyl cyanide (94% of theory); melting point: 32° C.

EXAMPLE 3

Analogously to Example 1 and in a corresponding 500 ml flask, 131 g (0.5 mol) of dimeric benzoyl cyanide and 5 g of sodium benzoate were dissolved in 113 g (0.5 mol) of benzoic acid anhydride and the solution was warmed to 160° C. under a water-pump vacuum (16 mbars). During this procedure, the benzoyl cyanide began to distil off. The internal temperature was increased slowly to 210° C., whereupon further benzoyl cyanide was distilled off.

Yield: 127 g of pure benzoyl cyanide (97% of theory); melting point: 32° C.

EXAMPLE 4

3 g of 1,4-diaza-bicyclo-(2.2.2)-octane were added to 262 g (1 mol) of dimeric benzoyl cyanide analogously to Example 1 and in a corresponding 500 ml flask. The reaction and working up were likewise carried out according to Example 1.

Yield: 234 g of pure benzoyl cyanide (89% of theory); melting point: 32° C.

COMPARISON EXAMPLE TO EXAMPLES 1 to 4

262 g (1 mol) of dimeric benzoyl cyanide were warmed to 200° C. for 2 hours without the addition of a basic compound. The reaction mixture was then distilled in vacuo.

Yield: 258 g of dimeric benzoyl cyanide ( 98% of theory); boiling point: 163° to 164° C. under 0.4 mbar; melting point: 96° to 97° C. (from methanol).

EXAMPLE 5

140.6 g (1 mol) of benzoyl chloride and 160 ml (4 mol) of hydrocyanic acid in 1,500 ml of dry ether were initially introduced into a 3 liter flask according to the statements in the literature (J. Chem. Soc. [London] 127, page 1,635 (1925)). 316.4 g (4 mol) of anhydrous pyridine were added dropwise at 0° to 10° C. in the course of 1 hour, whilst stirring. The reaction mixture was then kept at 0° to 10° C. for a further 12 hours. The pyridine hydrochloride which had precipitated was filtered off and washed with ether. The ether solutions were concentrated and small amounts of a precipitate were filtered off. After stripping off the solvent from the filtrate, 5 g of sodium cyanide were added to the reaction product which remained and the mixture was then warmed slowly to 160° to 165° C., and later to 200° to 210° C., under a water-pump vacuum, during which, finally, the entire amount of benzoyl cyanide was distilled off.

Yield: 118 g of pure benzoyl cyanide (90% of theory, relative to benzoyl chloride); boiling point: 92° to 95° C. under 18.6 mbars; melting point: 32° C.

COMPARISON EXAMPLE TO EXAMPLE 5

In a comparison experiment, a second reaction was carried out under the same conditions as described in Example 5. However, no sodium cyanide was added to the reaction product which was obtained by reacting benzoyl chloride with hydrocyanic acid and pyridine in ether and which remained after stripping off the solvent, but the product was subjected to fractional distillation in order to separate off the mixture of monomeric and dimeric benzoyl cyanide contained in the reaction product.

Yields: (I) 80 g of monomeric benzoyl cyanide (61% of theory), boiling point: 92° to 95° C. under 18.6 mbars;

(II) 39.1 g of dimeric benzoyl cyanide (32% of theory), boiling point: 163° to 164° C. under 0.4 mbars.

EXAMPLE 6

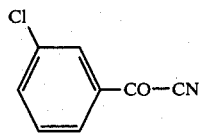

166 g (0.5 mol) of dimeric 3-chlorobenzoyl cyanide were heated to 180° C. in the presence of 3 g of sodium cyanide analogously to Example 1. By reducing the pressure to 16 mbars, monomeric 3-chlorobenzoyl cyanide began to distil over from the reaction mixture. During the distillation, the external temperature was increased slowly to 210° C. in order to bring the splitting of the dimer to completion.

Yield: 154 g of pure 3-chlorobenzoyl cyanide (93% of theory); boiling point: 118° to 120° C. under 18.6 mbars; melting point: 146° to 148° C. (from wash benzine).

EXAMPLE 7

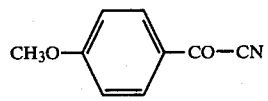

292 g (0.5 mol) of dimeric 4-methoxybenzoyl cyanide were warmed, in the presence of 3 g of sodium cyanide and under a water-pump vacuum (16 mbars), at first slowly to 180° C. and towards the end of the reaction to 210° C., analogously to Example 1. During this procedure, the monomeric 4-methoxybenzoyl cyanide formed slowly distilled over and solidified in the receiver.

Yield: 258 g of pure 4-methoxybenzoyl cyanide (88% of theory); melting point: 61° to 63° C.

EXAMPLE 8

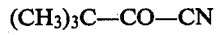

Analogously to Example 1 and in a corresponding 500 ml flask, 5 g of sodium acetate were added to 222 g (1 mol) of dimeric pivaloyl cyanide and the mixture was heated under normal pressure, first to 150° C. and then to 200° C. During this procedure, the monomeric pivaloyl cyanide formed was distilled off.

Yield 214 g of pure pivaloyl cyanide (96% of theory); boiling point: 121° C. (Under normal pressure).

EXAMPLE 9

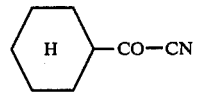

137 g (0.5 mol) of dimeric cyclohexanoyl cyanide (=cyclohexylglyoxylic acid nitrile) and 5 g of potassium acetate in 200 g of cyclohexanecarboxylic acid anhydride were heated slowly to 140° to 170° C. under a water-pump vacuum (18.6 mbars) analogously to Example 1, whereupon the monomeric cyclohexanoyl cyanide formed was distilled off. After further purification by subsequent fractional distillation, the following results were obtained:

Yield: 119 g of pure cyclohexanoyl cyanide (87% of theory); boiling point: 79° to 82° C. under 18.6 mbars.

Examples for the preparation of the starting materials (A) Dimeric benzoyl cyanide

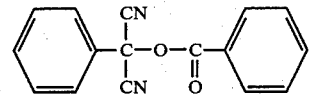

According to the statements in the literature (Ber. dtsch. chem. ges. 41, page 1,896 (1908)), 160 g (5.92 mol) of anhydrous hydrocyanic acid were added dropwise to 500 ml (6.32 mol) of anhydrous pyridine at 10° to 15° C., whilst stirring, and 832 g (5.92 mol) of benzoyl chloride were then added dropwise, whilst cooling. The reaction mixture was subsequently stirred for 1 hour and then left to stand overnight. 2 liters of 30% strength sulphuric acid were added to the solid mixture; the residue, which was insoluble in the acid, was filtered off and washed with 800 ml of 30% strength sulphuric acid. The residue on the filter was recrystallised from 2.5 liters of methanol.

Yield: 552 g of dimeric benzoyl cyanide (71% of theory); melting point: 96° to 97° C.

(B) Dimeric pivaloyl cyanide

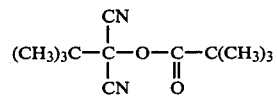

186 g (1 mol) of pivalic acid anhydride and 49 g of sodium cyanide were mixed and the mixture was warmed slowly to 120° C., whereupon a slightly exothermic reaction started. The reaction mixture became viscous.

The reaction mixture was subsequently heated to 150° C. for 1 hour and then cooled, and 300 ml of xylene were added. The insoluble material was filtered off and the filtrate was subjected to fractional distillation.

Yield: 91 g of dimeric pivaloyl cyanide (82% of theory); boiling point: 136° to 137° C. under 20 mbars; melting point: 54.5° to 55.4° C. (from isopropanol).

It will be understood that the specification and examples are illustrative but not limitative of the present invention and that other embodiments within the spirit and scope of the invention will suggest themselves to those skilled in the art.

What is claimed is:

1. A process for the preparation of a monomeric acyl cyanide of the formula

in which

R is optionally substituted alkyl of up to 8 carbon atoms and the substituents are selected from phenyl and naphthyl optionally substituted with alkyl, alkoxy, carbalkoxy and halogen; alkoxy or carboalkoxy of up to 4 carbon atoms in the alkoxy moiety; nitro; nitrile; and halogen;

cycloalkyl which has 5 or 6 carbon atoms in the ring system and optionally substituted with at least one of alkyl, alkoxy or carboalkoxy with up to 4 carbon atoms, nitro, nitrile and halogen;

phenyl or naphthyl optionally substituted with alkyl, alkoxy or carboalkoxy of up to 4 carbon atoms, nitro, nitrile and halogen;

a heterocyclic radical of 5 to 6 ring atoms which can include 1 to 3 hetero ring atoms selected from oxygen, sulfur and nitrogen;

a heterocyclic radical of 5 to 6 ring atoms fused to a benzene ring and which can include 1 to 3 hetero ring atoms selected from oxygen, sulfur and nitrogen; and a substituted heterocyclic radical of 5 or 6 ring atoms and 1 to 3 hetero atoms selected from oxygen, sulfur, nitrogen and at least one substituent selected from alkyl, alkoxy and carbalkoxy with, in each case, up to 4 carbon atoms, nitro, nitrile and halogen, which process comprises heating the corresponding dimeric acyl cyanide of the general formula $$R-\underset{\underset{CN}{|}}{\overset{\overset{CN}{|}}{C}}-O-\underset{\underset{O}{\|}}{C}-R, \quad (II)$$

in which R has the meaning stated above, to a temperature of from 50° to 300° C. in the presence of a basic compound and rapidly removing the monomeric acyl cyanide (I) formed from the reaction mixture.

2. Process as claimed in claim 1 wherein R is alkyl or substituted alkyl of up to 8 carbon atoms and the substituents are selected from phenyl and naphthyl optionally substituted with alkyl, alkoxy, carbalkoxy and halogen; alkoxy or carboalkoxy of up to 4 carbon atoms in the alkoxy moiety; nitro; nitrile; and halogen.

3. Process as claimed in claim 1 wherein R is cycloalkyl of 5 or 6 ring carbon atoms and optionally substituted with at least one of alkyl, alkoxy or carboalkoxy with up to 4 carbon atoms, nitro, nitrile and halogen.

4. Process as claimed in claim 1 wherein R is phenyl or naphthyl optionally substituted with alkyl, alkoxy or carboalkoxy of up to 4 carbon atoms, nitro, nitrile and halogen.

5. Process as claimed in claim 1 wherein R is a heterocyclic radical of 5 to 6 ring atoms with 1 to 3 hetero ring atoms selected from sulphur and nitrogen.

6. Process as claimed in claim 1 wherein R is a heterocyclic radical of 5 to 6 ring atoms fused to a benzene ring and including 1 to 3 hetero ring atoms selected from sulfur and nitrogen.

7. Process as claimed in claim 1 wherein R is a substituted heterocyclic radical of 5 or 6 ring atoms and 1 to 3 hetero atoms selected from sulfur, nitrogen and at least one substituent selected from alkyl, alkoxy and carbalkoxy with, in each case, up to 4 carbon atoms, nitro, nitrile and halogen.

8. Process as claimed in claim 1 wherein dimeric benzoyl cyanide is reacted with sodium cyanide to produce benzoyl cyanide.

9. Process as claimed in claim 1 wherein dimeric benzoyl cyanide is reacted with potassium cyanide, to produce benzoyl cyanide.

10. Process as claimed in claim 1 wherein dimeric benzoyl cyanide is heated in the presence of sodium cyanide, sodium benzoate and benzoic acid anhydride, to form benzoyl cyanide.

11. Process as claimed in claim 1 wherein dimeric benzoyl cyanide is heated in the presence of sodium cyanide and 1-4-diazabicyclo-2(2.2.2)-octane, to form benzoyl cyanide.

12. Process as claimed in claim 1 wherein benzoyl chloride is heated in the presence of hydrocyanic acid anhydrous pyridine and sodium cyanide, to form benzoyl cyanide.

13. Process as claimed in claim 1 wherein dimeric 3-chlorobenzoyl cyanide is heated in the presence of sodium cyanide, to form 3-chlorobenzoyl cyanide.

14. Process as claimed in claim 1 wherein dimeric 4-methoxybenzoyl cyanide is heated in the presence of sodium cyanide, to form 4-methoxybenzoyl cyanide.

15. Process as claimed in claim 1 wherein dimeric pivaloyl cyanide is heated with sodium acetate, to form pivoloyl cyanide.

16. Process as claimed in claim 1 wherein dimeric cyclohexanoyl cyanide is heated in the presence of potassium acetate and cyclohexanecarboxylic acid anhydride, to form cyclohexanoyl cyanide.

17. Process as claimed in claim 1 wherein the monomeric acyl cyanide is removed by distillation.

18. Process as claimed in claim 16 wherein the monomeric acyl cyanide is removed by distillation under vacuum.

19. Process as claimed in claim 1 wherein the reaction is carried out at a temperature between 80°–250° C.

20. Process as claimed in claim 18 wherein the reaction is carried out at a temperature between 100°–220° C.

21. Process as claimed in claim 1 wherein the reaction is carried out at a pressure of about 0.1 mbars.

22. Process as claimed in claim 1 wherein said compound having a basic reaction is employed in a catalytic amount.

23. Process as claimed in claim 1 wherein said compound having a basic reaction is employed in an amount of 0.01 to 0.2 mol per mol of dimeric acyl cyanide of the formula (II).

24. Process as claimed in claim 22 wherein said compound having a basic reaction is employed in an amount of 0.05 to 0.1 mol per mol of dimeric acyl cyanide of the formula (II).

25. Process as claimed in claim 1 wherein said dimeric acyl cyanide of the formula (II) is in the form of a mixture thereof with the corresponding monomeric acyl cyanide of the formula (I) obtained by reacting a carboxylic acid derivative with hydrocyanic acid in the presence of a basic catalyst.

26. Process as claimed in claim 1 wherein R is straight-chain or branched alkyl with 2 to 5 carbon atoms, which may optionally carry one or more substituents selected independently from aryl with 6 to 10 carbon atoms, which aryl may carry one or more substituents selected independently from $C_1$–$C_4$ alkyl, $C_1$–$C_4$ alkoxy, $C_2$–$C_4$ carbalkoxy and halogen; alkoxy with 1 to 4 carbon atoms, carbalkoxy with 1 to 4 carbon atoms in the alkoxy group, nitro, nitrile and halogen; cycloalkyl which has 5 or 6 carbon atoms in the ring system and which optionally may carry one or more substituents selected independently from alkyl, alkoxy and carbalkoxy with in each case up to 4 carbon atoms, nitro, nitrile and halogen; phenyl or naphthyl, either of which optionally may carry one or more substituents selected independently from alkyl, alkoxy and carbalkoxy with in each case up to 4 carbon atoms, nitro and halogen; or a 5-membered or 6-membered heterocyclic radical which can contain 1 to 3 hetero-atoms in the ring selected from oxygen, sulphur and nitrogen atoms, and can also be fused with a benzene ring, the heterocyclic radical optionally carrying one or more substituents selected independently from alkyl, alkoxy and carbalkoxy with in each case up to 4 carbon atoms, nitro, nitrile and halogen.

27. Process as claimed in claim 1 wherein basic compound is selected from alkali metal salts of aliphatic, cycloaliphatic and aromatic carboxylic acids; alkali metal cyanides and complex cyanides; tertiary amines; alkali metal hydroxides and alkaline earth metal hydroxides; and alcoholates and phenolates.

28. Process as claimed in claim 1 wherein basic compound is selected from sodium cyanide, potassium cyanide, sodium acetate, potassium acetate and sodium benzoate.

29. Process as claimed in claim 1 wherein the reaction is effected in the presence of an inert organic solvent.

30. Process as claimed in claim 28 wherein said inert organic solvent is acetic anhydride.

31. Process as claimed in claim 28 wherein said inert organic solvent is pivalic acid anhydride.

32. Process as claimed in claim 28 wherein said inert organic solvent is benzoic acid anhydride.

33. Process as claimed in claim 28 wherein said inert organic solvent is cyclohexanecarboxylic acid anhydride.

34. Process as claimed in claim 1 wherein said reaction is carried out continuously.

35. Process as claimed in claim 1 wherein said basic compound is selected from alkali metal salts of aliphatic, cycloaliphatic and aromatic carboxylic acids, alkali metal cyanides and complex cyanides, tertiary amines, alkali metal hydroxides and alkaline earth metal hydroxides or alcoholates or phenolates.

36. Process as claimed in claim 1 wherein said basic compound is selected from sodium acetate, sodium benzoate, the sodium salts of pivalic acid and of cyclohexylglyoxylic acid, triethylamine, dimethylbenzylamine, 1,4-diazabicyclo-(2.2.2)-octane, 1,8-diazabicyclo-(5.4.0)-undec-7-ene, 1,5-diaza-bicyclo-(4.3.0)-non-5-ene, pyridine, quinoline sodium hydroxide, potassium hydroxide, calcium hydroxide and barium hydroxide, sodium methylate sodium ethylate, potassium tert.-butylate, sodium phenolate, sodium cyanide, potassium cyanide, sodium acetate, potassium cyanide, sodium cyanide, sodium cyanozincate, potassium cyanozincate, sodium cyanocuprate, potassium cyanocuprate, potassium acetate, sodium benzoate, potassium benzoate, or the sodium salt or potassium salt of pivalic acid.

* * * * *